United States Patent [19]

Webster

[11] Patent Number: 4,541,426
[45] Date of Patent: Sep. 17, 1985

[54] DRESSING

[75] Inventor: David F. Webster, Bishops Stortford, England

[73] Assignee: Smith & Nephew Associated Companies p.l.c., England

[21] Appl. No.: 596,260

[22] Filed: Apr. 3, 1984

[30] Foreign Application Priority Data

Apr. 6, 1984 [GB] United Kingdom ............... 8309342

[51] Int. Cl.$^4$ ............................................. A61F 15/00
[52] U.S. Cl. ..................................................... 128/156
[58] Field of Search ................................ 128/155, 156

[56] References Cited

U.S. PATENT DOCUMENTS

| 3,543,750 | 12/1970 | Meizanis | 128/156 |
| 3,648,692 | 3/1972 | Wheeler | 128/156 |
| 3,790,433 | 2/1974 | Baron | 128/156 |
| 3,983,095 | 9/1976 | Bashaw et al. | 128/156 |
| 4,341,207 | 7/1982 | Steer et al. | 128/156 |

FOREIGN PATENT DOCUMENTS

| 0050514 | 4/1982 | European Pat. Off. | |
| 1492434 | 12/1969 | Fed. Rep. of Germany . | |
| 2015136 | 10/1971 | Fed. Rep. of Germany . | |
| 800572 | 8/1958 | United Kingdom . | |
| 815121 | 6/1959 | United Kingdom | 128/156 |
| 1203622 | 8/1970 | United Kingdom . | |
| 1280631 | 7/1972 | United Kingdom . | |
| 2061732 | 5/1981 | United Kingdom . | |

Primary Examiner—John D. Yasko
Assistant Examiner—Christa K. Scott
Attorney, Agent, or Firm—Jacobs & Jacobs

[57] ABSTRACT

A dressing suitable for application to lesions of the skin comprises a conformable apertured film. The film consists of two layers laminated together, the first layer which is the lesion contacting layer is formed from a material which swells in contact with water. The second layer does not swell or swells less than the first layer when in contact with water. When the first layer is placed in contact with a wet lesion the different swell characteristics causes the apertures to open allowing water to pass through the film from the wet surface to the top of the second layer. On a dry surface the apertures are closed. Preferably the apertures are in the form of slits. A composite dressing in which an absorbent for the fluid passing through the film is in contact with the second layer is also described.

40 Claims, 6 Drawing Figures

DRESSING

The invention relates to a dressing useful in treating lesions of the skin. More particularly this invention relates to a laminate dressing which has a reduced tendency to adhere to lesions of the skin.

It has long been a recognised problem that dressings are inclined to suffer from either or both the disadvantages that they sometimes tend to float away from a wound or else they sometimes tend to adhere to the wound surface.

The first of these disadvantages generally occurs when the wound is one that produces large volumes of exudate. Generally the method of overcoming this problem is to provide the dressing with holes so that the exudate can escape and the dressing remain in contact with the wound. Certain attempts to achieve this end are disclosed in U.K. Pat. Nos. 778813, 1298011, 1408345 and Patent Application Nos. 2061732 and 2074029. One successful dressing is Melolin (Trade mark, available from T. J. Smith & Nephew Ltd., Hull, U.K.) which comprises a perforated synthetic polymer film and an absorbent cellulosic pad. The perforated film is placed next to the exuding wound, the exudate passes through the perforations and is absorbed by the pad. A more recent suggestion has been to use a perforated polytetrafluoroethylene film in an effort to minimise the risk of any adherency of the dressing to the wound.

Alternatively dressings have been suggested which comprise a thin hydrophobic film laminated to a fibrous absorbent layer. The film contains a number of apertures in the form of slits. Such dressings are described in, for example, British Pat. Nos. 815,121 and 1,163,452 and U.S. Pat. No. 3,602,220. However dressings of that type have not been found to be satisfactory because either the slits do not open or do not open wide enough to allow passage of exudate through the film to the absorbent.

The second of the aforementioned disadvantages generally occurs when the wound has dried out due to lack of production of exudate. Generally the method of overcoming this problem is to provide the dressing with a continuous layer which retards the rate of loss of water. One effective method of achieving this end is described in British Pat. No. 1280631.

However none of the known methods are free of disadvantages since what may be an excellent dressing for one kind of wound will be unsuitable for many other wounds since wounds differ greatly in their output of exudate. It has now been realised that, not only is there a need for a dressing which is suitable for use on a number of different wound types, there is also a need for a dressing which can better cope with the variation in rate of exudate production from a given wound. A dressing has now been discovered which allows passage of a greater amount of exudate from a wound which produces greater amounts of exudate and which aids in allowing the wound to remain a moist wound when it produces only smaller amounts of exudate so that it does not float away from the moist surface and has a reduced tendency to adhere to the wound. The new dressing has been found to aid in the re-epithelialisation of the wound.

Accordingly the present invention provides a dressing suitable for applying to lesions of the skin which dressing comprises a conformable film with apertures therethrough characterised in that the film comprises a first layer laminated to a second layer, said first layer comprising a material which when in contact with water swells and said second layer comprising a material which when in contact with water does not swell or swells less than said first layer. It has been found that when in use on a wet surface the apertures of such dressings are enlarged and when not in use on a wet surface the apertures are not enlarged.

It is clear from the foregoing therefore that the present invention provides a dressing suitable for applying to lesions of the skin which dressing comprises a conformable film with apertures therethrough characterised in that the film comprises a first layer for contacting the lesion laminated to a second layer, said first layer comprising a material which when in contact with water swells and said second layer comprising a material which when in contact with water does not swell or swells less than said first layer whereby when in contact with a wet lesion the apertures open allowing water to pass through the film and when in contact with a dry surface the apertures are closed.

By "laminated" is meant that the first layer is attached to the second layer across the whole of their touching surfaces.

By a "wet surface" or "wet lesion" is meant a surface such as a wound upon which there is an aqueous liquid, for example water, blood, proteinaceous wound exudate or the like.

It is clear from the foregoing that dressings of the present invention are in a changing situation when placed in contact with an exuding wound. The apertures will open on absorption of water from the exudate by the first layer thereby allowing passage of exudate through the film; as the rate of exudate production decreases and the first layer starts to dry the apertures will close until, on a non-exuding wound, the apertures tend to regain or almost regain their original dimension. If the dressing is placed on unbroken normal skin, the apertures do not have the same tendency to open.

Whereas said first layer may be made of a mixture of different materials, it is preferred to use a single material. Normally said first layer is a plastic membrane and is preferably composed of a synthetic plastic. Similarly whereas said second layer may be made of a mixture of different materials, it is preferred to use a single material. Normally said second layer is a plastic membrane and preferably is composed of a synthetic plastic.

Suitably the first layer which contacts the wet surface of the lesion will be formed from a hydrophilic polymer. Aptly such a polymer will contain between 5 and 95% by weight water when hydrated, suitably between 8 and 60%, more suitably will contain between 10 and 50% water when hydrated and preferably will contain between 20 and 40% water when hydrated. Suitable polymers include cross-linked polyvinyl alcohol, cross-linked polyvinyl pyrrolidone, hydrophilic polyurethanes, hydrophilic hydroxyalkyl esters of poly(meth)acrylic aid and copolymers thereof, hydrophilic polyether-polyamide polymers, hydrophilic, water insoluble cellulosic derivatives such as cellulose acetate, cellulose acetate-proprionate which may be plasticised with, for example, polyhydric alcohols to make the films conformable. It is also envisaged that, although less favoured, films of blends of hydrophilic polymers are within the scope of this invention. Suitable blends include hydrophilic polyurethane with cellulosic derivatives, polyurethane with polyvinyl pyrrolidone, polyvinyl alcohol with polyvinyl pyrrolidone and blends of hydrophilic and hydrophobic polyether-polyamides. The suitable cross-linked polymers may be cross-linked either during the polymerisation reaction or afterwards using a polyfunctional group such as a polyisocyanate.

Particularly suitable hydrophilic polymers are cross-linked and linear hydrophilic polyurethanes. Preferred polyurethanes are those whose preparation is described in our copending British Application No. 2093190A at page 3 lines 16 to 74 which are incorporated herein by cross-reference. Preferred polyurethanes are linear polyether polyurethanes formed from polyethylene glycol, polypropylene glycol and a di-isocyanate and an ethanediol or ethylene diamine as chain extender. Preferred hydrophilic polyurethanes will contain from 20 to 40% by weight water when hydrated.

Also suitable for use in this invention are polyether-polyamide block copolymers whose preparation and properties have, for example, been described in British Pat. No. 1473972, French Pat. Nos. 1444437 and 2178205 and U.S. Pat. No. 3,839,243. A particularly apt polyether-polyamide block copolymer is known as Pebax 4011 RN00 available from ATO Chemical Products (U.K.) Limited. This polymer has a water content of about 55% when hydrated.

Preferably the polymer of the first layer is an elastomer and most preferably is a thermoplastic elastomer.

When the first layer of the wound dressing of the present invention is placed in contact with a wet surface, moisture is taken up into the layer and the layer swells and so expands. The second layer being non-swellable or less swellable does not expand as much as the first layer. It has been found that when the two layers are adhered over their surfaces the stress caused by differential swelling is relieved by the second layer deforming and by the apertures opening. When the apertures are opened exudate can more readily pass through the dressing. As the exudation diminishes the first layer becomes drier and tends to return to its unswollen state. The apertures thereby tend to close. The presence of the dressing will keep the surface of the wound moist which is believed to be beneficial to rapid wound healing.

The amount by which the first layer swells in contact with a wet lesion may be measured in terms of the linear expansion coefficient on hydration. This may be determined by placing two marks a known distance apart on the surface of an anhydrous piece of the appropriate polymer, allowing the polymer to hydrate in water for 24 hours and measuring the distance between the marks. The ratio of the latter to the former distances gives the required coefficient. Thus for hydrophilic polymers the following results have been obtained.

|  | Water content when hydrated | Coefficient of linear expansion |
| --- | --- | --- |
| Polyurethane | 28 | 1.10 |
| Polyurethane | 47 | 1.23 |
| Polyether-polyamide block copolymer | 55 | 1.35 |
| Polyurethane | 88 | 2.1 |

Desirably the material of the first layer has a coefficient of suitably 1.05 to 1.65, more suitably 1.08 to 1.50 amd preferably 1.10 to 1.40.

Similarly coefficients may be obtained for polymers which are suitable for forming the second layer.

|  | Coefficient of linear expansion |
| --- | --- |
| Polyurethane (Estane 5714F) | 1.00 |
| Polyvinyl chloride | 1.01 |
| Polyethylene | 1.00 |
| Polyester (Melinex) | 1.00 |
| Poly(styrene-butadiene-styrene) (Kraton 1101) | 1.01 |

Desirably the material of the second layer has a coefficient of 1.00 to 1.025, more suitably 1.00 to 1.015 and preferably 1.00 to 1.010.

Optionally the first layer may contain medicament. Suitable medicaments include broad spectrum antibacterial agents which may be released to the surface to which the dressing is applied. Suitable antibacterial agents include silver sulphadiazine, chlorhexidine salts and the like. Favoured antibacterial agents include salts of chlorhexidine such as its dihydrochloride, diacetate and digluconate.

The amount of antibacterial agent, for example a chlorhexidine salt, present in the first layer depends upon the expected water content of the layer, the time period over which the antibacterial agent is to be released and the solubility of the antibacterial agent in water. Clearly the higher the water content of the layer and the higher the solubility of the antibacterial agent the quicker it is relesed. However, typically medicated films of the present invention will contain up to 50% of an antibacterial agent such as a chlorhexidine salt, suitably the films will contain from 5 to 35% and preferably 10 to 25%.

The second layer will be formed from a polymeric material which does not swell or swells less than the first layer when in contact with water. The material should also be flexible so as to facilitate the opening of the apertures and is conformable so as to allow the layer to follow the contours of the body when in place over a lesion. Preferably the polymer material is an elastomer, especially a thermoplastic elastomer. Apt materials are those which have a low water content when hydrated. Suitably the material of the second layer will have a water content of less than 5%, more suitably is less than 3% and preferably of less than 1% by weight when hydrated.

Suitable polymers include polyolefins such as polyethylene, polyisobutylene, polyamides, polyesters, polyether polyesters, non-hydrophilic polyether-polyamides, plasticised polyvinyl chloride, styrene-butadiene block copolymers and styrene-isoprene block copolymers.

An apt polymer is polyurethane. Suitable polyurethanes include polyester and polyether polyurethanes examples of which are the Estanes (Registered trade mark of B.F. Goodrich Ltd). Suitable Estanes are those grades which are designated 5702, 5701, 5714F and 580201. Suitable polymers are polyolefins such as a polyethylene, polyisobutadiene, neoprene and the like. Such polymers may be advantageously used since films of appropriate thickness have a moisture vapour permeability which is less than that of the non-exuding wound so that when the apertures in such a film have closed the wound will not dry out.

Other particularly suitable polymers which have a low moisture vapour permeability are synthetic elastomers which include block copolymers of the styrene-butadiene or styrene-isoprene type. The copolymers may be either di-blocks or tri-blocks. Preferred polymers are those known as Kratons (Trade mark, available from Shell Chemicals Ltd.). A suitable Kraton is that designated Kraton 1101 which is a styrene-butadiene tri-block copolymer.

Other suitable polymers are the polyether polyester thermoplastic elastomers known as Hytrel (Trade mark, available from DuPont de Nemours & Co.). A preferred polyester is Hytrel 4056.

In a further aspect of the present invention the first layer may carry an adhesive on its surface which is to contact at least the skin surrounding the lesion. Suitable adhesives will comprise synthetic polymers. Such adhesives may be selected from those described in British Patent Specification No. 1280631 and European Patent Application No. 35399, both of which are incorporated herein by cross reference. The adhesive is applied to the dressing in a manner which will not prevent the apertures from opening or prevent the first layer from becoming wet by contact with the wound.

The dressings of this invention are most suitably sterile. Preferably the dressing of this invention is provided sealed within a bacteria-proof package. Such sterile dressings and such packages including the sterile dressing thus form favoured aspects of this invention. The dressing may be rendered sterile for example by irradiation Suitably the first layer will have a thickness of from 10 to 150 microns, more suitably 15 to 75 microns and preferably 20 to 50 microns, for example 25, 30 or 40 microns.

Suitably the second layer will have a thickness of 10 to 150 microns, more suitably 15 to 75 microns and preferably 20 to 50 microns, for example 25, 30 or 40 microns.

It is desirable to prevent the wound from drying out which is more easily achieved when the apertures are closed. To achieve this it is desirable that the rate of water loss through the second layer is less than that of the non-exuding wound. This aids the dressing in keeping the wound surface moist.

Normally and preferably the second layer employed in a dressing will be formed of a synthetic plastics material which when in the form of a continuous film of the thickness employed in the dressing has a moisture vapour permeability of not more than 1000 $gm^{-2}$ 24 $hrs^{-1}$ more suitably not more than 700 $gm^{-2}$ 24 $hrs^{-1}$ and yet more suitably not more than 500 $gm^{-2}$ 24 $hrs^{-1}$ and most suitably not more than 300 $gm^{-2}$ 24 $hrs^{-1}$, for example 25, 50, 100, 150 or 200 $gm^{-2}$ 24 $hrs^{-1}$. The moisture vapour permeablilty was measured at 37° C. with a relative humidity difference of 100% to 10% using the Payne Cup Method.

Although the thickness of each layer may vary within the limits as herein before described it is particularly advantageous in the dressings of the present invention if the combined thickness of the two layers is from 30 to 120 microns and the ratio of the thickness of the first layer to the second layer is from 3:1 to 1:1. Most preferably the thickness of the combined layers is 45 to 90 microns, for example 60 or 70 microns.

An adhesive may be applied over the entire surface of the first layer so that when in use the dressing is adhered to the intact skin surrounding the lesion but is not adhered to the wet surface of the lesion itself. When exudation ceases the surface of the lesion is still moist and the dressing remains non-adherent to that surface but adheres to the skin surrounding it thereby maintaining a bacteria-free envionment over the healing lesion. Alternatively the adhesive layer may be confined to a strip around the periphery of the dressing or to strips on two opposite edges of the dressing. This limited area of adhesive is not prefered.

If an adhesive layer is present, then the adhesive layer will suitably have a thickness of from 10 to 100 microns more suitably 15 to 75 microns and preferably 20 to 50 microns, for example 25, 30 or 40 microns.

Suitable adhesives include therefore polyvinyl ethyl ether adhesives and acrylate surgical adhesives especially those formed from the polymerisation of 47 parts 2-ethyl hexyl acrylate, 47 parts butylacrylate and 6 parts acrylic acid, in acetone solution.

The adhesive may be applied to the first layer to give a continuous or discontinuous layer, by methods described in, for example, British Pat. Nos. 1280631 and 819,635 in such a manner as not to prevent the slits from opening. Preferably the adhesive layer is in the form of a layer which extends over the surface of the first layer but which does not prevent the apertures from opening.

The apertures will be so arranged that when the first layer is placed in contact with a wet surface, for example an exuding wound, the apertures will open to allow the passage of the exudate through the dressing. Such exudate will normally be absorbed in an absorbent which will normally be present in contact with the second layer.

This absorbent may be a gauze or cellulosic pad or a synthetic polymer foam or the like.

The apertures may have measurable breadthwise dimension as well as lengthwise dimension and more suitably will have only a small breadthwise dimension in comparison to their lengthwise direction (for example less than 10% as broad as long, more suitably less than 2% as broad as long and most suitably less than 1% as broad as long).

Favourably the apertures may be in the form of slits, which may be unconnected or which may connect (for example to form crosses or putative flaps). Normally the apertures will be in the form of slits which are unconnected. The slits may be straight or arcuate. The slits are usually arranged in rows and often in rows in which the slits of any one row will be staggered from those on the next row. Alternatively the slits of one row may be at right angles to those of the adjacent row or the slits may be in the form of patterns such as crosses or stars but in which the slits are not interconnected but remain discrete. Suitably the slits will be from 3 to 15 mm long, more suitably will be from 5 to 12 mm long and preferably 6 to 10 mm long for example 7 mm long. The slits in any row will suitably be from 1 to 15 mm apart, more suitably 3 to 10 mm apart and preferably 4 to 8 mm apart for example 5 or 7 mm apart. The distance between slits of adjacent rows will suitably be 1 to 15 mm, more suitably 3 to 10 mm and preferably 4 to 8 mm.

Alternatively some apertures may interact so that when opened they will be in the form of flaps. Suitably the flaps may be rectangular, square, triangular, semicircular and the like in shape. One side of the geometric figure will remain attached to the remainder of its layer, so that the flap may open when in contact with a wet surface and be closed when not in contact with a wet surface. The dimensions of the flaps will be such that the exudate from an exuding wound can pass through at a rate which prevents pooling of exudate under the dressing but does not dry out the wound. Suitably the area encompassed by the flap will be 1 to 50 mm², more suitably 2 to 30 mm² and preferably 4 to 20 mm².

To illustrate the effect of water upon the film of the invention, a piece of the film was placed with the hydrophilic layer against the surface of a wet sponge or foam. After a few seconds the slits began to open and within a few minutes the slits had opened sufficiently to allow water to pass through the film from the sponge. When the system had reached equilibrium conditions, a photograph of the surface of the second layer of the laminate was taken and enlarged at known magnification. Using these photographs it was possible to calculate the area of each slit when open. As the various patterns and slit dimensions provided equally varied values for the area of an open slit, the open area per unit area was then calculated. Suitably, when open the slit will form from 2 to 20% of the surface of the laminate, more suitably 3 to 15% of the surface of the laminate and preferably will form 5 to 12% of the surface of the second layer of the laminate, for example 10%.

Alternatively the required open area per unit area may be achieved by the use of a great many slits of short length which are arranged very close together. Typically such slits will be 0.5 to 3 mmm in length, more aptly 0.6 to 2 mm in length, favourably 0.7 to 1.5 mm in length, more favourably 0.8 to 1.2 mm in length and preferably 1 mm in length and usually spaced from each other at a distance of 0.7 to 2 mm, more suitably 0.8 to 1.5 mm, preferably 1 mm. The length of the slit will be sufficient to prevent the hydrophilic polymer layer from resealing after perforation. It is a considerable surprise that such small slits can be employed. It has proved particularly advantageous to use these small apertures since they llow for readier flow of exudate through the dressing while maintaining a low level of adherency of the dressing to wounds.

Suitably the absorbent will be applied to the dressing of the present invention immediately after it has been placed on the wound. The absorbent and the dressing may be then held in place on the skin using adhesive tape or bandage or the like in any convenient manner. However, another aspect of the present invention envisages a composite dressing in which the dressing as hereinbefore described is combined with an absorbent material to form a non-adherent absorbent dressing having an apertured laminate wound contacting layer as hereinbefore described which has apertures which are open when in contact with a wet surface and are closed when not in contact with a wet surface. The absorbent material may be adhered to the wound dressing by adhesive (but not in such a manner as to prevent the opening and closing of the apertures) or may adhere in other conventional manner such as spot welding or the like.

Suitably the absorbent may be a gauze or cellulose pad or a synthetic polymer foam particularly a hydrophilic polymer foam. The presence of the first and second apertured layers which open and close depending on the wetness of the wound or lesion prevents any fibers of a fibrous absorbent like a cellulosic pad adhering to the wound.

In another version of the composite dressing of this invention, the outer surface of the absorbent material is provided with a layer of film which aids in preventing contamination of the wound. The outer layer of film is preferably bacteria proof. The outer layer of film preferably has a significant permeability to moisture vapour, for example greater than 500 gm$^{-2}$ 24 hrs$^{-1}$ more suitably greater then 1000 gm$^{-2}$ 24 hrs$^{-1}$ most suitably greater than 2000 gm$^{-2}$ 24 hrs$^{-1}$ and preferably greater than 3000 gm$^{-2}$ 24 hrs. Suitably the outer layer is made of a microporous material such as Porvic (Trade mark) (microporous polyvinylchloride) or a microscopically continuous but moisture vapour permeable material such as polyurethane or other material hereinbefore said to be suitable for the first layer.

The outer layer may be bonded to the absorbent in any convenient manner such as, casting, spot welding or by employing an adhesive. If an adhesive is employed it may be discontinuous or continuous but should have a suitably high permeability to moisture vapour, (for example it may be one of the adhesives hereinbefore described) and be disposed to provide the preceeding permeability.

In one particularly suitable form of this aspect of the invention the outer layer may extend beyond the absorbent to provide a surrounding projecting film locating the dressing for example by means of an adhesive suitable for adhering a dressing to the skin.

An alternative less favoured aspect of the present invention comprises a dressing suitable for applying to lesions of the skin which dressing comprises a conformable film with apertures therethrough characterised in that film comprises a first layer laminated to a second layer and a third layer laminated to the second layer, said first and third layer comprising material which when in contact with moisture swell and said second layer which when in contact with moisture does not swell or swells less than said first layer, whereby when said first layer is placed on a wet surface the apertures are enlarged and when in use on a dry surface the apertures are not enlarged. Normally the first and third layers will be formed from the same material and comprise those polymers as described hereinbefore. Wound dressings of this type will be stiffer than the two layer dressing described above but will still be conformable especially when all layers are made of elastomer.

Dressings of the present invention may be made by placing a layer of the non-swellable or less-swellable polymer onto a release surface such as a silicone release paper (either by casting from solution, or by cutting a pre-formed film to the appropriate shape) and then the swellable layer is cast thereon from a suitable non-aqueous solution of the appropriate polymer in its non-hydrated form. The solvent is removed by passage through an oven or the like. The release surface serves as a carrier for the laminate so that the hot polymers are not stretched or otherwise distorted during the solvent removal.

The apertures are formed in the resultant laminate most suitably by using a series of pointed knife blades arranged in a block at a predetermined separation. The laminate may then be cut to the appropriate size and packaged and sterilised in conventional manner.

The smaller sized slits, that is 0.5 to 3 mm, may be formed in the laminate by means of a sewing-machine type of device in which the needle is replaced by a blade of the appropriate length. The laminate is advanced automatically after each slit is formed and the slits are more easily arranged in straight rows.

The preferred dressings of the present invention will be described with reference to the accompanying drawings in which.

Figure 1:
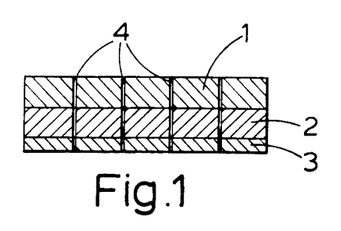
FIGS. 1 to 3 show a cross-section through a dressing.

FIG. 1 shows a simple form of the dressing of this invention. The first layer (1) is formed from a water swellable polymeric material, such as hydrophilic polyurethane and is laminated to the second layer (2) which is formed from a non-swellable polymeric material. The second layer (2) is carried on a release paper (3) (which aids in handling the dressing prior to use). Slits (4) are shown passing through the two layers (and also through the release paper which is an aid to manufacture). In use the release paper is removed and the dressing placed onto a wet wound with layer (1) against the wound. As the layer (1) absorbs water the slits (4) open to permit passage of wound exudate through the opening, for example to an absorbent placed in contact with layer (2) (not shown).

Figure 2:
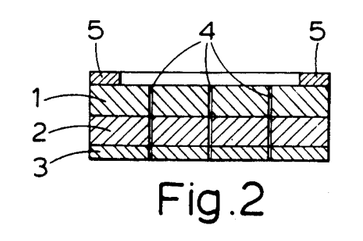

FIG. 2 shows a wound dressing which has a layer of adhesive (5) along two opposing edges whereby the dressing may be adhered to the skin. The adhesive on the periphery of the dressing does not effect the operation of slits (4).

Figure 3:
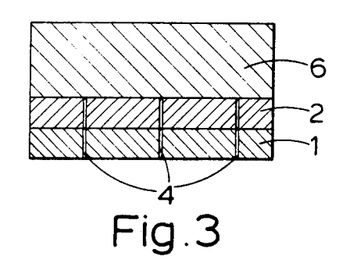

FIG. 3 shows a composite dressing in which an absorbent layer (6) is present in contact with layer (2).

Figure 4:
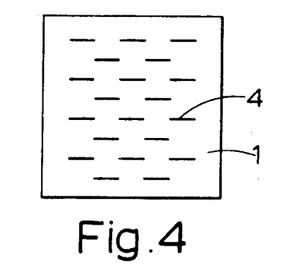
FIGS. 4 to 6 show arrangements of differently formed apertures suitable for use in dressings of the invention.
Figure 5:
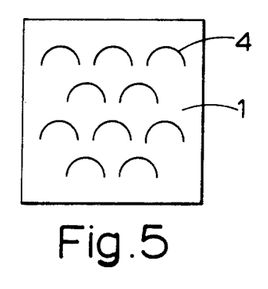
Figure 6:
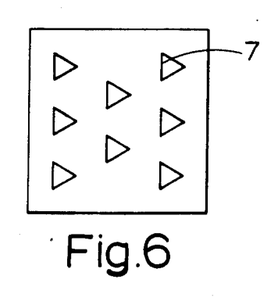

FIGS. 4 to 6 show alternative arrangements for the slits and flaps. in FIG. 4 (a preferred form) the slits are shown as staggered rows of linear slits whilst FIG. 5 shows the slits as having arcuate shape. In FIG. 6 the openings form two sides of triangular flaps which remain attached to their respective layers by side (7) the other two sides being adapted to allow the flap to open when placed on a wet wound.

EXAMPLE 1

A film formed from a styrene-butadiene-styrene triblock copolymer was obtained at a thickness of 31 microns. The polymer grade used to form this film is known as Kraton 1101 and the film is referred to hereinafter as Kraton film.

A hydrophilic polyurethane (as described in Example 2 of British Patent Application No. 2093190 which contains approximately 26% of water when hydrated) in its anhydrous state was dissolved in industrial methylated spirits to give a 15% w/v solution.

This solution was cast onto a silicone release paper to give a film 7.5 cm wide having a weight per unit area of 30 gsm (approx). The solvent was evaporated by passage through a hot oven in a conventional manner.

The two films, Kraton 1101 and hydrophilic polyurethane were then heat laminated together by passing through heated rollers at 85° C. (approx), in conventional manner to form a strip of two component films 7.5 cm wide supported by the silicone release paper. The strip was then cut to provide squares of film laminate (7.5 cm×7.5 cm.

The dressing was provided with apertures using a block which had protruding from it pointed knife blades arranged in a pattern of staggered alternate rows with 3 mm between the rows and 15 mm between the tips of each knife blade in each row. The block was placed on the laminate to perforate both films and release paper and then drawn forward for 10 mm to form the slits in the laminate.

To illustrate the effect of water upon the slits the silicone release paper was peeled off the laminate and the laminate placed with the hydrophilic layer against the surface of a wet sponge. After a few seconds the slits began to open. Within a few minutes the slits were sufficiently open to allow water to pass through the dressing from the sponge. The dressing was removed from the sponge and placed on a dry surface whereupon the slits slowly closed again.

By using a coloured liquid in the sponge and by placing an absorbent pad such as cotton wool above the dressing it is possible to detect coloured liquid passing through the slits into the absorbent.

EXAMPLE 2

A wound dressing was prepared in a similar manner to that as described in Example 1 except that a polyethylene film (pretreated by high voltage high frequency electric discharge) having a weight per unit area of 25 gsm was used in place of the Kraton film. The polyethylene film was carried on a silicone release paper to prevent distortion and stretching during the solvent removal stage.

The wound dressing so prepared, when perforated, performed effectively but somewhat less so than that of Example 1.

EXAMPLE 3

A 25 micron thick film of a polyether-polyamide (Pebax 4011 RN OO), extruded in the conventional manner as a flat film, may be heat laminated to a 25 micron thick film of polyisobutadiene, extruded in the conventional manner as a flat film, by passing through heated rollers in conventional manner. The two layer composite may have slits provided therein in the manner of Example 1. The thus formed dressing allows more liquid to pass therethrough the wetter the surface upon which it rests.

EXAMPLE 4

A polyurethane syrup comprising 100 parts of Estane 5714F (available from B. F. Goodrich Ltd), 240 parts tetrahydrofuran and 160 part of acetone was cast onto a silicone release paper to give a film 7.5 cm wide having thickness 30 microns.

A hydrophilic polyurethane (as described in Example 2 of British patent application No. 2093190 which contains approximately 26% water when hydrated) in its anhydrous state was dissolved in industrial methylated spirits to give a 15% w/w solution. This was cast onto the Estane film and the solvent removed to give a thickness of 30 microns. The laminate film was cut into strips in the conventional manner. The film when tested in the manner described in Example 1 allowed water to pass through it when placed on a wet surface. (Analagous products were made by heat laminated).

EXAMPLES 5–10

A series of dressings according to the invention were prepared either using the same method as in Example 1 for the hydrophilic polyurethane/styrene-butadiene-styrene laminate or as in Example 4 for the hydrophilic polyurethane/polyurethane laminates. The apertures in the films were in the form of slits arranged in parallel rows, the slit length was 7 mm and the slits were 5 mm apart. Each film was placed with the hydrophilic layer against a wet foam and the opening of the slits followed using a microscope. The following films which show varied water content and thickness of the hydrophilic layer gave satisfactory dressings.

| Example | First layer Hydrophilic polyurethane Water content (wt hydrated) | Thickness (Microns) | Second layer 30 microns thick |
|---|---|---|---|
| 5 | 25 | 60 | Polyurethane (5714F) |
| 6 | 25 | 120 | " |
| 7 | 30 | 30 | " |
| 8 | 45 | 30 | " |
| 9 | 25 | 60 | Poly(styrene-butadiene-styrene) |
| 10 | 45 | 30 | Poly(styrene-butadiene-styrene) |

EXAMPLE 11

A film of a polyether polyester elastomer, (Hytrel 4056) (available from E. I. DuPont de Nemours & Co.) was prepared by extrusion of the polymer onto a siliconised release surface at a melt temperature of 204° C. The film was then passed between a pair of nip rollers to give a film of thickness 37.5 micron.

A film of hydrophilic polyurethane was prepared by the method described in Example 1. The polyester film and polyurethane film were laminated together in the conventional manner and a series of slits were made through the laminate using the pattern described in Example 5.

The slit containing laminate was placed with the hydrophilic film layer in contact with water and the slits rapidly opened. The laminate was removed from contact with water and the slits slowly closed.

EXAMPLE 12

A film of plasticised polyvinyl chloride was laminated to a film of hydrophilic polyurethane prepared according to the method of Example 1. The two films were each approximately 30 microns thick.

The laminate was slit using the pattern described in Example 5 and the hydrophilic film layer placed in contact with water when the slits opened. Upon removal from the wet surface the slits closed.

EXAMPLE 13

A film of polyamide (nylon-6, Platilon) (Trade mark) was laminated by means of heat and pressure to a film of hydrophilic polyurethane formed according to the method described in Example 1. The laminate was then slit with a pattern of slits as described in Example 1. The thickness of the polyamide film was 15 microns. The laminate was placed with the hydrophilic film layer in contact with water and the slits opened. On removal from the water the slits closed.

EXAMPLE 14

A film of a polyester was laminated to a hydrophilic polyurethane film prepared as described in Example 1. The resultant laminate film had slits placed through it by cutting with knife blades in the pattern described in Example 5. The thickness of the polyester film was 25 microns.

The laminate was placed with the hydrophilic film layer in contact with water and the slits through the film opened. On removal from the water the slits slowly closed.

EXAMPLE 15

A film of polyvinylidine dichloride was laminated to a film of a hydrophilic polyurethane prepared by the method described in Example 1. Slits were placed through the laminate in the pattern described in Example 5.

The laminate was placed with the hydrophilic film layer in contact with water and the slits through the film opened. This effect was reversed when the laminate was removed from the water.

EXAMPLE 16

A three layer dressing was formed by making a two-layer film as described in Example 4 and laminating a further layer of hydrophilic polyurethane onto the other side of the polyurethane (Estane) film. A pattern of slits was cut through all three layers using an array of sharp blades in a pattern described in Example 5.

One of the hydrophilic polyurethane surfaces of the laminate was placed in contact with water. The slits on all three layers opened and water was able to pass through the laminate film. The laminate was removed from the water and the slits were observed to close.

EXAMPLE 17

An acetone solution was prepared by dissolving an acrylic ester copolymer formed by the polymerisation of 47 parts n-butyl acrylate, 47 parts of 2-ethylhexyl acrylate and 6 parts acrylic acid in acetone, in the solvent to give a 15% solution. This solution was cast onto a silicone release paper using a doctor blade and the solvent allowed to evaporate at room temperature. The adhesive layer formed had a coating weight per unit area of 30 gsm. The adhesive layer was transfer coated to a Kraton film by passing beteen a pair of nip rollers at room temperatue. A film of plasticised regenerated cellulose acetate (Rayophane 400 PVT 177, Trade mark, available from British Sidac Ltd) 25 microns thick was then attached to the Kraton film by means of the adhesive layer coated onto the Kraton film above by passing the two films through a pair of nip rollers. A pattern of slits was cut through the laminate using an array of sharp blades giving a pattern of slits which was the same as that described in Example 5. Reinsertion of the blades was used to ensure the slits were free of adhesive.

The laminate was placed with the regenerated cellulose acetate layer in contact with the water. The layer absorbed water and the slits opened. On removal from the water the slits slowly closed.

EXAMPLE 18

A film of polyvinyl alcohol (Polyviol W28/20 (Trade mark, available from Wacker-Chemie GmbH) was cast from a 12% aqueous solution. The film was dried at 60° C. The resulting film was 38 microns thick and cold water-insoluble but capable of absorbing water.

The polyvinyl alcohol film was laminated to a polyurethane film in a similar manner to that described in Example 4. A pattern of slits was cut through the laminate using an array of sharp blades giving a pattern which is the same as that described in Example 1.

The laminate was placed with the polyvinyl alcohol layer in contact with water. The slits through the films opened. The slits closed on removal from the water.

EXAMPLE 19

An adhesive solution was prepared from an acrylic ester copolymer 47 parts n-butyl acrylate, 47 parts of 2-ethylhexyl acrylate and 6 parts acrylic acid polymerised in acetone, by dissolving the polymer in acetone to give a 15% solution. This solution was pattern spread onto a silicone release paper (Steralease 77 (Trade Mark)) using a patterned roller and the solvent removed. The adhesive coating had a coating weight per unit area of 30 gsm. The adhesive layer was laminated to a film comprising a hydrophilic polyurethane layer and a Kraton polymer layer prepared as described in Example 1 by passage between a pair of rollers at room temperature.

A pattern of slits was cut through the release paper, adhesive layer, hydrophilic polyurethane layer and Kraton layer using an array of sharp blades giving a pattern described in Example 4.

The silicone release paper was removed and the adhesive side of the dressing placed in contact with water. The slits in the film opened.

EXAMPLE 20

A dressing was prepared in a similar manner to that described in Example 19 except that the adhesive solution was formed from an acrylic polymer/water emulsion (Primal N 580, available from Rohm and Haas) (80 g).

The slits opened when the dressing was placed in contact with water.

EXAMPLE 21

An adhesive solution was prepared from an acrylic ester copolymer of 47 parts n-butyl acrylate, 47 parts 2-ethylhexyl acrylate and 6 parts acrylic acid polymerised in acetone, and dissolved in acetone to give a 15% solution. The solution was coated in a pattern onto a silicone release paper and the solvent removed. This adhesive layer was laminated to a film comprising a hydrophilic polyurethane layer and a Kraton polymer layer prepared as described in Example 1 by passage between a pair of rollers.

A pattern of slits was cut through the adhesive strip so formed in such a way that the uncoated areas of the hydrophilic polyurethane/Kraton film were cut leaving the adhesive layer intact.

The silicone release paper was removed and when the hydrophilic polyurethane was placed in contact with water the slits opened.

EXAMPLE 22

A dressing similar to that described in Example 21 was prepared except that the adhesive layer was present as a narrow strip around the periphery of the hydrophilic polyurethane.

The slits opened when the hydrophilic polyurethane layer was placed in contact with water.

EXAMPLE 23

An apertured film was prepared according to the method described in Example 1. To the surface of the Kraton film layer was lightly adhered a conventional cellulosic fibrous absorbent material by means of spots of adhesive.

The hydrophilic film layer of the composite dressing was placed in contact with water which had been coloured green with a lissamine dye. As the hydrophilic layer swelled the slits opened and water passing through the slits was observed to have coloured the absorbent.

EXAMPLE 24

A composite dressing was formed in a similar manner to that described in Example 23. A microporous polyvinyl chloride film carrying on one surface a porous acrylate pressure sensitive adhesive was adhered to the absorbent. The microporous film was larger in area than the composite dressing so that an adhesive margin was left around the periphery of the microporous film.

The hydrophilic film layer was contacted with coloured water held in a foam layer, the adhesive margin of the microporous film being adhered to a metal plate surrounding the foam layer. The dressing was left in place for 2 hours and then removed. It was observed that coloured water had flowed through the slits in the film and been absorbed by the absorbent material.

EXAMPLE 25

A hydrophilic polyurethane was formed by the polymerisation of polyethylene glycol, polypropylene glycol and 1,4 di-isocyanato cyclohexane and ethylene diamine as chain extender in methylene chloride. A film made from the resultant polymer had a water content when hydrated of about 24%.

A solution of the polymer in methylene chloride was mixed with chlorhexidine dihydrochloride first by hand and then at high shear to remove any residual lumps. The resultant mixture was cast in a conventional manner onto a silicone release paper and the solvent removed to give a film containing 15% w/w of chlorhexidine dichloride in the film and a weight per unit area of 32 gsm.

This film was laminated to a Kraton film in the usual way. A pattern of slits was cut through the resultant laminate to give a pattern which was the same as that described in Example 5.

The laminate was placed with the hydrophilic polyurethane layer in contact with water. The slits opened and on removal from the water the slits closed.

A further sample of the laminate was left in contact with a known volume of water for a period of 24 hours. The water was removed and the chlorhexidine dichloride content determined by analysis. A further volume of water was then contacted with the hydrophilic layer and the analysis repeated. This extract test was repeated over four days. The amount of chlorhexidine dihydrochloride released cumulatively per day in microgrammes/cm$^2$ was 210 microgrammes, 480 microgrammes and 600 microgrammes.

EXAMPLE 26

A composite dressing was formed in a similar manner to that described in Example 24 except that the absorbent layer was a flexible open cell hydrophilic polyurethane foam (Hypol FHP 2002, Trade mark, available from W. R. Grace & Co.).

EXAMPLE 27

An extruded film of a mixture of 70 parts polyester polyurethane and 30 parts polyether-polyamide (Pebax 4011 RN OO) was formed at weight per unit area of 40 gsm.

This film was laminated to a polyurethane film (Estane 5714F) formed as described in Example 4, by passing the two films through a pair of nip rollers at 85°–90° C.

A pattern of slits was cut through the laminate of films using an array of sharp blades arranged as described in Example 5.

A piece of the laminate films was placed with the blend film in contact with water and the slits were observed to open. When the laminate was removed from contact with water, the slits were observed to close.

EXAMPLE 28

A film formed from a styrene-butadiene-styrene triblock copolymer was obtained at a film weight per unit area of 30 gsm. The polymer grade used to form this film was Kraton 1101.

A hydrophilic polyurethane (prepared in the manner described in Example 2 of British Patent Application No. 2093190 and which contains approximately 25% by weight of water when hydrated) in its anhydrous state was dissolved in industrial methylated spirits to give a 15% w/w solution.

This solution was cast onto a silicone release paper to give a film 7.62 cm (3 in.) wide having a weight per unit area of 30 gsm after removal of the solvent by passage through a hot oven in a conventional manner.

The two films, Kraton 1101 and hydrophilic polyurethane were then heat laminated together by passing through heated rollers at 85° C. (approx), in a conventional manner to form a strip of film having two layers and supported on a siliconised release paper. The resulting strip was then cut to provide squares of film, 7.62 cm×7.62 cm (3 in×3 in).

The film was provided with apertures in the form of slits using a sowing machine with a flat blade, 1 mm long in place of the more conventional needle. The sowing machine enabled a row of slits to be cut through the film and release paper 1 mm long and 1 mm from each other in the row as the machine automatically advanced the film between each cut. A second row of slits was placed adjacent to the first row and 2 mm from it. The slits in adjacent rows were in line and not staggered.

By repeating this process several rows of slits 1 mm long were cut across the film. A margin of uncut film 6 mm long were cut across the film. A margin of uncut film 6 mm (approx) wide was left to provide stability to the film and to prevent the risk of initiating tearing.

To illustrate the effect of water upon the slits the silicone release paper was peeled off the laminate and the laminate placed with the hydrophilic layer against the surface of a wet sponge. After a few seconds the slits were observed to be opening. Within a few minutes the slits were sufficiently open to allow water to pass through the film from the sponge. The dressing was removed from the sponge and placed on a dry surface whereupon the slits slowly closed.

EXAMPLES 29–42

In Examples 29 to 42 films comprising two layers were formed in a similar manner to those described in Examples 2 to 15 respectively. The films were provided with slits in the same manner as described in Example 28 so that the slits were 1 mm in length, 1 mm apart in each row and 2 mm betwen adjacent rows.

These apertured films were placed with they hydrophilic layer in contact with water and the slits were observed to open to allow passage of water through the film. On removing from the water the slits were observed to close.

All these dressings may be sterilised in a conventional manner and packaged in bacteria proof packs until required.

I claim:

1. A dressing suitable for application to lesions of the skin which dressing comprises a conformable film having apertures therethrough which open and close said film comprising a first layer for contacting the lesion laminated to a second layer, said first layer comprising a material which when in contact with water swells and said second layer comprising a material which when in contact with water does not swell or swells less than said first layer whereby when in contact with a wet lesion the apertures open allowing water to pass through the film and when in contact with a dry surface the apertures are closed.

2. A dressing according to claim 1 wherein the dressing further comprises an absorbent layer in contact with the second layer.

3. A dressing according to claim 2 wherein the dressing further comprises a bacteria-proof, moisture vapour permeable, liquid impervious film layer in contact with the absorbent layer.

4. A dressing according to claim 1 in which the first layer has a linear expansion coefficient on hydration of from 1.05 to 1.65 and the second layer has a linear expansion coefficient on hydration of from 1.00 to 1.025.

5. A dressing according to claim 1 in which the first layer is formed from a hydrophilic polymer which will contain from 10 to 50% by weight of water when hydrated and is from 15 to 75 microns in thickness.

6. A dressing according to claim 1 in which the hydrophilic polymer is a linear polyether polyurethane which will contain from 20 to 40% by weight water when hydrated and have a thickness of from 25 to 75 microns.

7. A dressing according to claim 1 in which the second layer is formed from a synthetic polymer which has a water content of less than 5% by weight when hydrated and a thickness of from 15 to 75 microns.

8. A dressing according to claim 1 in which the moisture vapour permeability of the second layer is less than 500 $gm^{-2} 24\ hr^{-1}$ at 37° C. and 100% to 10% relative humidity.

9. A dressing according to claim 1 in which the first layer contains a broad spectrum antibacterial agent.

10. A dressing according to claim 1 in which the apertures are in the form of slits from 3 to 15 mm long spaced 1 to 15 mm from each other.

11. A dressing according to claim 1 in which the apertures are in the form of slits from 0.5 to 3 mm in length, spaced 0.7 to 2 mm from each other.

12. A dressing according to claim 11 in which the slits are from 0.6 to 2 mm in length and are spaced 0.8 to 1.5 mm from each other.

13. A dressing according to claim 1 in which the first layer has on its lesion facing surface a skin-compatible pressure sensitive adhesive formed from a synthetic polymer.

14. A dressing according to claim 13 in which the adhesive is present on the periphery of the dressing and comprises a polyvinyl ethyl ether adhesive or an acrylate ester copolymer adhesive.

15. A dressing according to claim 3 in which the bacteria-proof moisture vapour permeable, liquid impervious film layer has a moisture vapour permeability of greater than 1000 $gm^{-2} 24\ hr^{-1}$ at 37° C. and 100 to 10% relative humidity difference.

16. A dressing according to claim 1 in which the dressing is in sterile form and packaged in a bacteria-proof pack.

17. A dressing according to claim 4 in which the first layer is formed from a hydrophilic synthetic polymer which will contain from 10 to 50% by weight of water when hydrated and said layer is from 15 to 75 microns in thickness.

18. A dressing according to claim 17 in which the second layer is formed from a synthetic polymer which has a water content of less than 5% by weight when hydrated and said layer is from 15 to 75 microns thick.

19. A dressing according to claim 18 in which the first layer is a hydrophilic polyurethane.

20. A dressing according to claim 18 in which the second layer is a polyolefine, polyamide, polyester, polyurethane, polyvinyl chloride, styrene-butadiene block copolymer or styrene-isoprene block copolymer.

21. A dressing according to claim 18 in which the second layer is a synthetic elastomer selected from block copolymers of styrene-butadiene or styrene-isoprene.

22. A dressing according to claim 1 in which the apertures are in the form of slits.

23. A dressing according to claim 4 in which the apertures are in the form of slits.

24. A dressing according to claim 17 in which the apertures are in the form of slits.

25. A dressing according to claim 18 in which the apertures are in the form of slits.

26. A dressing according to claim 19 in which the apertures are in the form of slits.

27. A dressing according to claim 20 in which the apertures are in the form of slits.

28. A dressing according to claim 21 in which the apertures are in the form of slits.

29. A dressing suitable for application to lesions of the skin which dressing consists essentially of a conformable film having apertures therethrough which open and close, said film comprising a first layer for contacting the lesion laminated to a second layer, said first layer comprising a synthetic polymer which has a linear expansion coefficient on hydration of 1.05 to 1.65 and said second layer comprising synthetic polymer which has a linear expension coefficient on hydration of 1.00 to 1.025, whereby said apertures are larger when said dressing is on a wet surface than when not on a wet surface.

30. A dressing according to claim 29 in which the first layer has a linear expension coefficient on hydration of 1.00 to 1.50.

31. A dressing according to claim 30 in which the first layer is a polyurethane which has a water content of from 20 to 40% by weight when hydrated.

32. A dresssing according to claim 29 in which the apertures are in the form of slits from 3 to 15 mm long spaced 1 to 15 mm from each other.

33. A dressing according to claim 29 in which the apertures are in the form of slits from 0.5 to 3 mm in length spaced 0.7 to 2 mm from each other.

34. A sterile dressing which dressing is suitable for application to lesions of the skin and which dressing has apertures which open and close which dressing consists essentially of a conformable film having apertures in the form of slits therethrough said film comprising a first layer for contacting the lesion laminated to a second layer, said first layer comprising a synthetic polymer which when in contact with water swells with a linear coefficient of expansion on hydration of 1.05 to 1.65 and said second layer comprising synthetic elastomer which when in contact with water does not swell or swells less than said first layer with a linear coefficient of expansion of 1.00 to 1.025 whereby when in contact with a wet lesion the slits open allowing water to pass therethrough and when in contact with a dry surface the slits close.

35. A dressing according to claim 34 wherein said first layer has a coefficient of 1.08 to 1.50 and said second layer has a coefficient of 1.00 to 1.015.

36. A dressing according to claim 34 wherein said first layer has a coefficient of 1.10 to 1.40 and said second layer has a coefficient of 1.00 to 1.010.

37. A dressing according to claim 34 wherein said first layer is a hydrophilic polyurethane.

38. A dressing according to claim 35 wherein said first layer is a hydrophilic polyurethane which contains 20–40% water by weight when hydrated.

39. A dressing according to claim 34 wherein the slits are arranged in rows.

40. A dressing according to claim 36 wherein the thickness of the dressing is from 45 to 90 microns.

* * * * *